United States Patent [19]

Meybeck et al.

[11] Patent Number: 5,716,800
[45] Date of Patent: Feb. 10, 1998

[54] **ANTI-ACNE COMPOSITION CONTAINING A *PORIA COCOS* WOLF EXTRACT**

[75] Inventors: Alain Meybeck; Frédéric Bonte, both of Courbevoie, France

[73] Assignee: LVMH Recherche, France

[21] Appl. No.: 581,502

[22] PCT Filed: Jun. 29, 1994

[86] PCT No.: PCT/FR94/00786

§ 371 Date: Dec. 27, 1995

§ 102(e) Date: Dec. 27, 1995

[87] PCT Pub. No.: WO95/01159

PCT Pub. Date: Jan. 12, 1995

[30] Foreign Application Priority Data

Jun. 30, 1993 [FR] France ................... 93 07967

[51] Int. Cl.⁶ ........................................... C12P 33/00
[52] U.S. Cl. ................... 435/52; 435/254.1; 435/911; 552/540; 552/546
[58] Field of Search .................. 552/540, 546; 435/52, 911, 254.1

[56] References Cited

U.S. PATENT DOCUMENTS 3,010,878  11/1961  Pan et al. ..................... 435/52
3,369,032  2/1968   Diassi et al. ................. 552/540

FOREIGN PATENT DOCUMENTS 60-078910  5/1985   Japan.
60-258104  12/1985  Japan.
64-038010  8/1989   Japan.

OTHER PUBLICATIONS

"Review Bulletin de la Societe Chimique de France" (1980, No. 9–10, pp. 473–477).
"Japan Journal of Pharmacology" (1992), vol. 59 (1), pp. 89–96.
"Studies on Antinephritic Effects of Plant Component of *Poria cocos* Wolf on Original–Type Anti–GBM Nephritis in Rats".

*Primary Examiner*—Terressa Mosley
*Attorney, Agent, or Firm*—Bierman, Muserlian and Lucas

[57] ABSTRACT

The invention concerns the use of an organic or hydro-organic extract of *Poria cocos* Wolf fungi for the preparation of a cosmetic and/or pharmaceutical composition, in particular a dermatological composition, for the treatment of acne and oily skin.

The preferred concentration of *Poria cocos* extract is in the range 0.001% to 5% by weight with respect to the total weight of the final composition.

Cosmetic or pharmaceutical compositions, in particular dermatological compositions, can be prepared for the effective treatment of acne and oily skin.

36 Claims, No Drawings

ANTI-ACNE COMPOSITION CONTAINING A *PORIA COCOS* WOLF EXTRACT

The present invention essentially concerns the use of a *Poria cocos* Wolf fungus extract for the preparation of a cosmetic or pharmaceutical composition, in particular a dermatological composition, for the treatment of acne or oily skin, and a cosmetic treatment method.

The article in "Revue Bulletin de la Société Chimique de France" (1980, No. 9–10, pp 473–477) describes the use of *Poria cocos* Wolf fungus extracts, more particularly triterpenes contained in these extracts, which have cytotoxic activity for the treatment of tumors.

Further, the database Excerpta Medica contains an English abstract of the Japanese review "Japan Journal of Pharmacology" (1992), volume 59 (1), pp 89–96, which describes an antinephritic activity in a *Poria cocos* Wolf fungus extract.

Still further, published Japanese application number JP-A-1/038010 POLA describes a cosmetic composition for encouraging hair restoration and hair growth containing, among a number of active ingredients, an organic extract, in particular an alcoholic extract, of *Poria cocos* Wolf fungi.

Within the context of the present invention, we have unexpectedly discovered that organic or hydro-organic extracts of *Poria cocos* Wolf fungi exhibit a novel anti-ache activity and an oily skin controlling activity.

The aim of the present invention is thus to solve the novel technical problem with a solution which provides novel cosmetic or pharmaceutical formulations, in particular dermatological compositions, with an anti-acne and/or oily skin control activity in a simple, reproducible, inexpensive manner which can be used on an industrial scale and cosmetically and/or pharmaceutically.

The present invention satisfactorily solves this novel technical problem for the first time.

In a first aspect, therefore, the present invention concerns the use of an organic or hydro-organic extract of *Poria cocos* Wolf fungi for the manufacture of a cosmetic and/or pharmaceutical composition, in particular a dermatological composition, for the treatment of acne and oily skin.

Within the context of the invention, the expression "hydro-organic extract" means an extract obtained from a mixture of water and an organic solvent which is miscible with water. In particular, within the context of the present invention, a hydro-alcoholic mixture is preferably used, such as a hydro-ethanolic or a hydro-methanolic mixture, again preferably containing at least 50% by weight of alcohol with respect to the total weight of the hydro-alcoholic mixture.

In a particular embodiment, an alcoholic extract is used, in particular an entirely ethanolic extract, or a hydro-alcoholic extract such as a hydro-ethanolic or hydro-methanolic extract of *Poria cocos* Wolf.

In another particular embodiment, the concentration of *Poria cocos* extract is in the range 0.001% to 5% by weight with respect to the total weight of the final composition.

In yet another particular embodiment, the extract is at least partially incorporated into hydrated lamellar lipid phases or into liposomes.

In a still further particular embodiment, the *Poria cocos* extract is combined with at least one other active ingredient, preferably selected from the group consisting of a seboregulatory substance, an antiseptic substance, an anticomedo substance and an anti-inflammatory substance.

In still another particular embodiment, the seboregulatory substance is an extract of licorice, glycyrrhiza glabra.

In a further particular embodiment, the antiseptic substance is an anti-corynebacterium substance such as hexamidine diisethionate, which is commercially available, an isodon japonicus extract, which is commercially available, clindamycin, or erythromycin.

In still another particular embodiment, the anticomedo substance is selected from the group consisting of acid vitamin A, vitamin A and its derivatives such as the acetate, palmirate, propionate and azelaic acid.

In still another particular embodiment, the anti-inflammatory substance is selected from the group consisting of ammonium glycyrrhyzinate, glycyrrhetinic acid, a-bisabolol, tocopherol phosphate and a corticoid.

In a second aspect, the present invention also concerns a method for the cosmetic treatment of oily skin, characterized in that an effective quantity of an organic or hydro-organic extract of *Poria cocos* Wolf fungi is topically applied to the oily zones of the skin, the effective quantity generally being in a cosmetically or dermatologically acceptable excipient.

In a particular implementation, a cosmetic composition containing 0.001% to 5% by weight of the *Poria cocos* Wolf extract is applied.

In a further particular implementation, a cosmetic composition containing an alcoholic extract, in particular an entirely ethanolic extract, or a hydro-alcoholic extract such as a hydro-ethanolic or a hydro-methanolic extract of *Poria cocos* Wolf fungi is applied.

In a still further particular implementation, the *Poria cocos* Wolf extract is at least partially incorporated into hydrated lamellar phases or into liposomes.

Other aims, characteristics and advantages of the invention will become clear from the following description made with reference to various examples and activity tests, given simply by way of illustration and which does not in any way limit the scope of the invention.

In one or other of the preceding aspects of the invention, the organic extraction solvent is preferably an alcoholic extract, in particular selected from the group consisting of methanol, ethanol, butyleneglycol and propyleneglycol. These solvents can advantageously be used alone or in a mixture. They may also be used mixed with water. Some extracts are commercially available, in particular a butyleneglycol extract of *Poria cocos* Wolf sold by the Japanese company Maruzen under the trade name Hoelen BG.

It should also be noted that for any of the preceding aspects of the invention, the extract can be conventionally formulated in cosmetic or pharmaceutical compositions, in particular dermatological compositions, for example in the form of a gel, cream, emulsion or milk, for the treatment of oily skin or skin subject to acne, or for the treatment of acne.

Unless otherwise indicated, the percentages are given by weight, in particular in the examples and in the claims.

EXAMPLE 1

Manufacture of an Ethanolic Extract of *Poria cocos* Wolf Fungi

Commercially available *Poria cocos* Wolf fungus was ground to increase its contact surface with the solvent. This base material was extracted at 40° C. with ethanol using a base material/solvent proportion of 20 g/l to 100 g/l. The extract was concentrated under vacuum.

This extract was termed extract $I_1$ of the invention.

EXAMPLE 2

Establishing the Inhibiting Activity of a *Poria cocos* Wolf Extract on 5a-reductase Enzyme, an Enzyme Involved in Acne and Oily Skin This test was based on the method of inhibiting 5a-reductase enzyme, which transforms testosterone to dihydrotestosterone, described in the review J. I. D., (1987), 89, pp 87–92.

The skilled person is well aware that the formation of dihydrotestosterone from testosterone, in particular under the action of 5a-reductase enzyme, is involved in acne and oily skin and that inhibition of this enzyme can effectively combat acne and oily skin. Thus establishing, for any active ingredient, a significant inhibition of 5a-reductase enzyme activity is an appropriate test for determining an anti-acne and oily skin control activity. Further, this test is recognized by the skilled person as being reliable in in vitro tests carried out using the method described in the literature cited above.

In accordance with the literature, the test used an inoculum of normal human prepuce fibroblasts.

This fibroblast inoculum was cultured in a E 199 C medium (Techgen, France) to which 1% of foetal calf serum was added, in a proportion of 10000 fibroblast cells per microplate hole. 0.1 µCi of testosterone labelled with tritium was also added to each of these holes, to identify the metabolites formed in contact with the fibroblasts by measuring their radioactivity.

Some holes acted as references and only received 1 ml of a 0.1% DMSO solution, with no active ingredient. The other holes received the active ingredient to be tested, in this case an ethanolic extract of *Poria cocos* Wolf obtained as described in Example 1, in 1 ml of a 0.1% DMSO (dimethylsulfoxide) solution.

In each case, either for the reference or the active ingredient to be tested, the contact time with the culture was 24 hours.

After 24 hours, the supernatant liquid was recovered, and the steroids were extracted with 1 ml of an ethyl acetate-cyclohexane (1/1 by volume) extraction solvent. The extracted steroids were deposited on a commercial thin layer chromatography plate (Kieselgel 60F 254 DC Alu from Merck®. The eluting system for the plate was a chloroform-methanol mixture, 98/2 volume/volume.

A scanner from Berthold, France, adapted to receive thin layer chromatography plates, was used to measure the radioactivity of the spots corresponding to testosterone and dihydrotestosterone.

The results are summarised in Table I.

TABLE I

| Product | Testosterone | Dihydro-testosterone | Activity A (%) |
| --- | --- | --- | --- |
| Reference (0.1% DMSO) | 47 ± 3% | 28 ± 1% | 0 |
| Product $I_1$ of the invention from Example 1 (50 µg/l) | 61 ± 4% | 20 ± 1% | 29% |

Activity A was determined using the following formula:

$$A = \frac{Tr - Te}{Te} \times 100$$

where:

Tr represents the percentage of testosterone measured after 24 hours of culture of the sample treated with the product from Example 1 (ethanolic extract of *Poria cocos* Wolf in accordance with the invention, in 0.1% DMSO);

Te is the percentage of testosterone measured in the reference sample which received only 0.1% DMSO, also after 24 hours of culture.

It is clear from Table I that the alcoholic *Poria cocos* Wolf fungus extract had a significant activity for inhibiting 5a-reductase enzyme, correspondingly inhibiting the transformation of testosterone to dihydrotestosterone and thus rendering this extract of particularly use for the treatment of ache and oily skin.

EXAMPLE 3

Establishing the Seboregulatory Activity of Compositions of the Invention in Man It is known that oily skin, even when not covered with ache, has a shiny and unsightly appearance due to the excessive production of sebum.

The present experiment in man aimed to show the activity of compositions in accordance with the invention in regulating the secretion of sebum.

Three preparations, the compositions of which are shown in Table II below, were tested.

Preparation B was a spray, preparation G was a cleansing gel and preparation S was an oil control lotion.

TABLE II

Composition of tested preparations (percentages by weight)

| | B(spray) | G(gel) | S(lotion) |
| --- | --- | --- | --- |
| Commercial butyleneglycol Poria cocos Wolf extract (Hoelen BG) | 0.3 | 0.06 | 3.6 |
| Commercial isodon Japonicus extract | 0.15 | 0.03 | 1.8 |
| Hydro-ethanolic Scutellaria baicalensis extract (*Ichimaru Pharcos*) | 0.05 | 0.01 | 0.6 |
| Corn starch | 0 | 0 | 8.0 |
| Cosmetic excipient | qsp100.— | qsp100.— | qsp100. |

The experiment was carried out on 12 volunteers of average age 33 years, who had oily skin which was not subject to ache.

1. Evaluation of oil control effect

Before the experiment began, no cosmetics were used for a period of three days.

The oil control effect of regulating lotion S was evaluated after application to half the face of a standard quantity, using a syringe.

Seborrhea and brightness of the skin were measured using a sebumeter and a chromameter respectively.

a-Sebumetry

A SM 810 Pc sebumeter from Courage and Khazaka was used.

The quantities of lipids at the cutaneous surface of the forehead were measured by sebumetry. The current level and the rate of sebaceous excretion 30 minutes after degreasing were expressed as lipid indices.

The current level was measured before applications and every 2 hours over a period of 8 hours to observe the kinetics.

The comparative results, expressed in lipid indices, are shown in Table III

TABLE III

Kinetic study of seborrhea after treatment

| | untreated side | treated side |
|---|---|---|
| Time zero (application) | 6.83 ± 3.71 | 7.50 ± 3.86 |
| 2 h after application | 117.70 ± 46.13 | 88.67 ± 34.21 |
| 4 h after application | 165.40 ± 39.33 | 147.83 ± 42.01 |
| 6 h after application | 203.90 ± 22.88 | 176.63 ± 26.63 |
| 8 h after application | 213.67 ± 30.00 | 181.70 ± 35.21 |

The difference between the lipid indices obtained with the untreated reference zone and the treated zone was significant at 2 hours, and was maintained at 4 hours, 6 hours and 8 hours.

It is clear from Table III that the application of regulating lotion S in accordance with the invention significantly reduces the skin re-oiling after cleansing. The maximum current level was reached in 6 hours.

b-Chromametry

The skin brightness of a treated cheek and an untreated cheek was measured at the level of the corner of the nose by chromametry using a Minolta CR 200 Chromameter before application and then every 2 hours over 8 hours.

The comparative skin brightness results are shown in Table IV.

TABLE IV

Skin brightness after treatment

| | untreated side | treated side |
|---|---|---|
| Time zero (application) | 62.41 ± 2.19 | 62.60 ± 1.88 |
| 2 h after application | 62.31 ± 1.93 | 62.16 ± 2.22 |
| 4 h after application | 62.28 ± 1.71 | 61.79 ± 1.59 |
| 6 h after application | 62.09 ± 1.73 | 61.41 ± 1.60 |
| 8 h after application | 62.25 ± 1.82 | 61.73 ± 2.10 |

The brightness parameter L on the treated side showed a reduction which was constant for the first 6 hours.

These developments are all statistically significant with respect to the corresponding value at the moment of application of the preparation of the invention (time zero).

In conclusion, these tests have clearly demonstrated that the preparation of the invention had an immediate effect, from its first application, reducing the excessive flow of sebum and attenuating the brightness of the skin, compared with the untreated skin zones.

2. Improvement in skin condition

The three preparations B, G and S were applied twice a day to the forehead. Cleansing was carried out with gel G followed by spraying with spray B then application of lotion S. The treatment was continued for 30 days.

The improvement in the skin condition of 12 volunteers, all with oily skin which was not subject to acne, was evaluated before, during and at the end of a treatment period of 30 days.

A first improvement evaluation was made after 15 days of treatment, and a second after 30 days.

The intensity of seborrhea was divided into four levels:
level zero: practically no seborrhea
level 1 : low intensity seborrhea
level 2 : medium intensity seborrhea
level 3 : high intensity seborrhea Table V below summarises the observations made on the 12 subjects:

TABLE V

Distribution of treated subjects before, during and at the end of the treatment as a function of the intensity of seborrhea

| | Before use | After 15 days of use | after 30 days of use |
|---|---|---|---|
| Level 0 | 0 | 0 | 0 |
| Level 1 | 0 | 4 | 9 |
| Level 2 | 10 | 8 | 3 |
| Level 3 | 2 | 0 | 0 |

We observed an overall displacement within the group from the high intensity classes to the low intensity classes: the disappearance after 15 days of subjects at level 3, a gradual reduction during the test of the numbers in level 2 and increase in level 1, which was in the majority at the end of the test.

A more precise analysis of the individual results from case to case, considering also intra-level developments, indicated the following:

after 15 days of treatment:

stationary state: 2 cases reduction by one level: 5 cases slight reduction (intra-level): 5 cases after 30 days of treatment:

stationary state: 1 case reduction by one level: 8 cases slight reduction (intra-level): 3 cases These clinical results, based on determining the current level of intensity of sebum (before degreasing for measuring the rate) strongly favor the treatment: at the end of the test, 8 subjects out of 12 had a notably reduced level of seborrhea. The improvement was less substantial with 3 subjects, and only one case appeared not to have been affected by the treatment.

Thus the preparations of the invention are highly effective in man for treating oily skin by regulating the production and flow of sebum. Their use thus contributes to improving the condition of the skin. The skin becomes healthier and has a more pleasing appearance.

Examples will be given below of cosmetic or pharmaceutical compositions, in particular dermatological compositions, using a *Poria cocos* Wolf extract in accordance with the present invention.

EXAMPLE 4

Cosmetic Composition in the Form of a Treatment Gel

This cosmetic composition contained the following ingredients, by weight:

| | |
|---|---|
| commercial butyleneglycol Poria cocos Wolf extract from Hoelen BG | 0.5 g |
| isodon extract (antiseptic) | 0.5 g |
| ammonium glycyrrhizinate as an anti-inflammatory substance | 0.3 g |
| Crémophor RH 40R | 1 g |
| Carbopol 940R | 1 g |
| fragranced aqueous excipient containing preservative | qsp 100 g |

The extracts were added with the Crémophor RH 40® to the water to form 50% of the composition, which was added to a gel of 2% Carbopol containing fragrances and preservatives, to form the final composition with the above formula.

The gel was applied twice a day to blackheads on skin with a tendency to suffer from acne until the skin condition became good, namely after about three weeks.

EXAMPLE 5

Cosmetic Composition in the Form of a Cleansing Lotion

This composition had the following ingredients:

| | |
|---|---|
| ethanolic extract of Poria cocos as in Example 1 | 0.1 g |
| hexamidine diisethionate | 0.1 g |
| hyaluronic acid (moisturising substance) | 0.1 g |
| glycerin | 0.2 g |
| fragranced aqueous excipient containing preservative | qsp 100 g |

The ingredients were mixed together to obtain a homogeneous lotion which was used for twice-daily cleansing of oily skin.

This lotion was applied in the evening to zones of oily skin, after removing any makeup, as a preventative treatment and/or to treat the skin.

EXAMPLE 6

Dermatological Anti-Acne Composition

This composition had the following ingredients:

| | |
|---|---|
| retinoic acid | 0.05 g |
| Poria cocos extract $I_1$ from Example 1 | 0.5 g |
| clindamycin phosphate | 1 g |
| propyleneglycol | 5 g |
| ethanol | 30 g |
| gelled excipient containing Carbopol 940 ™ and preservative | qsp 100 g |

This composition was prepared by firstly dissolving the different ingredients in ethanol to which the gelled excipient was added. The composition could be used to pat onto local acne lesions until the lesions disappeared.

We claim:

1. A method for the cosmetic treatment of oily areas of the skin, comprising topically applying to the oily areas of the skin an effective amount of an organic or hydro-organic extract of *Poria cocos* Wolf fungi in a cosmetically or dermatologically acceptable excipient.

2. A method according to claim 1, characterized in that a cosmetic composition containing 0.001% to 5% by weight of the *Poria cocos* Wolf extract is applied.

3. A method according to claim 1, comprising applying a cosmetic composition containing an alcoholic extract, or a hydro-alcoholic extract of *Poria cocos* Wolf fungi.

4. A method according to claim 1, characterized in that the *Poria cocos* Wolf extract is at least partially incorporated into hydrated lamellar phases or into liposomes.

5. A method according to claim 1, characterized in that the *Poria cocos* extract is combined with at least one other active ingredient, selected from the group consisting of a seboregulatory substance, an antiseptic substance, an anticomedo substance and an anti-inflammatory substance.

6. A method according to claim 5, wherein the seboregulatory substance is an extract of licorice.

7. A method according to claim 3, wherein the antiseptic substance is an anti-corynebacterium substance.

8. A method according to claim 5, wherein the anticomedo substance is selected from the group consisting of acid vitamin A, vitamin A, vitamin A esters and azelaic acid.

9. A method according to claim 5, characterized in that the anti-inflammatory substance is selected from the group consisting of ammonium glycyrrhyzinate, glycyrrhetinic acid, a-bisabolol, tocopherol phosphate and a corticoid.

10. A method for performing a skin treatment for acne, said method comprising:
administering to an affected skin area an effective amount for said treatment purpose of an organic or hydro-organic extract of *Poria cocos* wolf fungi.

11. The method of claim 10, wherein said *Poria cocos* Wolf extract is topically applied to said skin area.

12. The method of claim 10, wherein said *Poria cocos* wolf extract is applied to said affected skin area as a dermatological composition containing 0.001% to 5% by weight of the *Poria cocos* wolf extract in a dermatological acceptable excipient.

13. The method of claim 10, wherein said *Poria cocos* Wolf extract is applied to said affected skin area as a dermatological composition containing an alcoholic extract or a hydro-alcoholic extract of *Poria cocos* Wolf fungi in a dermatological acceptable excipient.

14. The method of claim 13, wherein said alcoholic extract is an ethanolic extract and said hydro-alcoholic extract is selected from the group consisting of a hydro-ethanolic extract and a hydro-methanolic extract.

15. The method of claim 10, wherein said *Poria cocos* Wolf extract is at least partially incorporated into hydrated lamellar phases or into liposomes.

16. The method of claim 10, wherein said *Poria cocos* Wolf extract is combined with at least one active ingredient selected from the group consisting of a seboregulatory substance, an antiseptic substance, an anticomedo substance and an anti-inflammatory substance.

17. The method of claim 16, wherein said seboregulatory substance is an extract of licorice.

18. The method of claim 16, wherein said antiseptic substance is an anti-corynebacterium substance.

19. The method of claim 18, wherein said anti-corynebacterium substance is selected from the group consisting of hexamidine diisethionate, an isodon japonicus extract, clindamycin and erythromycin.

20. The method of claim 16, wherein the anticomedo substance is selected from the group consisting of acid vitamin A, vitamin A, vitamin A esters, and azelaic acid.

21. The method of claim 20, wherein said vitamin A esters are selected from the group consisting of vitamin A acetate, vitamin A palmitate and vitamin A propionate.

22. The method of claim 16, wherein said anti-inflammatory substance is selected from the group consisting of ammonium glycyrrhyzinate, glycyrrhetinic acid, a-bisabolol, tocopherol phosphate and a corticoid.

23. The method of claim 3, wherein said alcoholic extract is an entirely ethanolic extract and said hydro-alcoholic extract is selected from the group consisting of a hydro-ethanolic extract and a hydro-methanolic extract.

24. The method of claim 7, wherein said anti-corynebacterium substance is selected from the group consisting of hexamidine diisethionate, an isodon japonicus extract, clindamycin and erythromycin.

25. The method of claim 5, wherein said vitamin A esters are selected from the group consisting of vitamin A acetate, vitamin A palmitate and vitamin A propionate.

26. An anti-ache composition for topical application to skin comprising an effective amount to treat ache of an organic or hydro-organic extract of *Poria cocos* Wolf fungi, said *Poria cocos* Wolf extract being combined with at least one active ingredient selected from the group consisting of a seboregulatory substance, an antiseptic substance, an anti-comedo substance and an anti-inflammatory substance; and a dermatologically topical acceptable excipient.

27. The anti-ache composition of claim 26, wherein said seboregulatory substance is an extract of licorice.

28. The anti-ache composition of claim 26, wherein said antiseptic substance is an anti-corynebacterium substance.

29. The anti-ache composition of claim 28, wherein said anti-corynebacterium substance is selected from the group consisting of hexamidine diisethionate, an isodon japonicus extract, clindamycin and erythromycin.

30. The anti-ache composition of claim 26, wherein the anticomedo substance is selected from the group consisting of acid vitamin A, vitamin A, vitamin A esters, and azelaic acid.

31. The anti-ache composition of claim 30, wherein said vitamin A esters are selected from the group consisting of vitamin A acetate, vitamin A palmirate and vitamin A propionate.

32. The anti-ache composition of claim 26, wherein said anti-inflammatory substance is selected from the group consisting of ammonium glycyrrhyzinate, glycyrrhetinic acid, a-bisabolol, tocopherol phosphate and a corticoid.

33. The anti-acne composition of claim 26, wherein said amount of *Poria cocos* wolf extract in said composition is 0.001% to 5% by weight composition.

34. The anti-ache composition of claim 26, wherein said *Poria cocos* Wolf extract is an alcoholic extract or a hydro-alcoholic extract of *Poria cocos* Wolf fungi.

35. The anti-ache composition of claim 26, wherein said alcoholic extract is an ethanotic extract and said hydro-alcoholic extract is selected from the group consisting of a hydro-ethanolic extract and a hydro-methanolic extract.

36. The anti-ache composition of claim 26, wherein said *Poria cocos* Wolf extract is at least partially incorporated into hydrated lamellar phases or into liposomes.

\* \* \* \* \*

UNITED STATES PATENT AND TRADEMARK OFFICE
CERTIFICATE OF CORRECTION

PATENT NO.   : 5,716,800
DATED        : February 10, 1998
INVENTOR(S)  : A. Meybeck et al.

It is certified that error appears in the above-identified patent and that said Letters Patent is hereby corrected as shown below:

Column 9,
Change "anti-ache" to -- anti-acne --.
Line 10, change "anti-ache" to -- anti-acne --.
Line 12, change "anti-ache" to -- anti-acne --.
Line 14, change "anti-ache" to -- anti-acne --.
Line 19, change "anti-ache" to -- anti-acne --.

Column 10,
Line 1, change "anti-ache" to -- anti-acne --.
Line 3, change "anti-ache" to -- anti-acne --.
Line 5, change "anti-ache" to -- anti-acne --.
Line 10, change "anti-ache" to -- anti-acne --.
Line 12, change "anti-ache" to -- anti-acne --.
Line 15, change "anti-ache" to -- anti-acne --.
Change "claim 26" to -- claim 34 --.
Line 16, change "ethanotic" to -- ethanolic --.
Line 19, change "anti-ache" to -- anti-acne --.

Signed and Sealed this

Twenty-ninth Day of January, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 5,716,800
DATED         : February 10, 1998
INVENTOR(S)   : A. Meybeck et al.

It is certified that error appears in the above-identified patent and that said Letters Patent is hereby corrected as shown below:

Column 9,
Line 1, change "anti-ache" to -- anti-acne --.
Line 10, change "anti-ache" to -- anti-acne --.
Line 12, change "anti-ache" to -- anti-acne --.
Line 14, change "anti-ache" to -- anti-acne --.
Line 19, change "anti-ache" to -- anti-acne --.

Column 10,
Line 1, change "anti-ache" to -- anti-acne --.
Line 3, change "palmirate" to -- palmitate --.
Line 5, change "anti-ache" to -- anti-acne --.
Line 10, change "wolf" to -- Wolf --.
Line 12, change "anti-ache" to -- anti-acne --.
Line 15, change "anti-ache" to -- anti-acne --.
Line 15, change "claim 26" to -- claim 34 --.
Line 16, change "ethanotic" to -- ethanolic --.
Line 19, change "anti-ache" to -- anti-acne --.

This certificate supersedes Certificate of Correction issued January 29, 2002

Signed and Sealed this

Sixth Day of August, 2002

Attest:

JAMES E. ROGAN
Attesting Officer    Director of the United States Patent and Trademark Office